US011793333B2

(12) United States Patent
Rahmani et al.

(10) Patent No.: US 11,793,333 B2
(45) Date of Patent: Oct. 24, 2023

(54) BED COVERING SYSTEM

(71) Applicants: Ali Rahmani, Fort Myers, FL (US); Patricia Rahmani, Fort Myers, FL (US)

(72) Inventors: Ali Rahmani, Fort Myers, FL (US); Patricia Rahmani, Fort Myers, FL (US)

(*) Notice: Subject to any disclaimer, the term of this patent is extended or adjusted under 35 U.S.C. 154(b) by 80 days.

(21) Appl. No.: 17/000,560

(22) Filed: Aug. 24, 2020

(65) Prior Publication Data

US 2022/0053952 A1 Feb. 24, 2022

(51) Int. Cl.
*A47G 9/02* (2006.01)
*A61M 21/00* (2006.01)

(52) U.S. Cl.
CPC .......... *A47G 9/0215* (2013.01); *A47G 9/023* (2013.01); *A47G 9/0207* (2013.01); *A47G 9/0223* (2013.01); *A41D 2400/10* (2013.01); *A61M 2021/0066* (2013.01); *D10B 2401/04* (2013.01); *D10B 2503/06* (2013.01); *Y10S 5/923* (2013.01)

(58) Field of Classification Search
CPC ........ A47G 9/023; A47G 9/02; A47G 9/0238; A47G 9/0223; A47G 9/0207; A47G 9/0284; A61M 2021/0066; Y10S 5/923; D03D 13/004; D03D 13/008; D10B 2401/04; D10B 2503/06; A41D 2400/10; A41D 31/065; Y10T 428/23957
See application file for complete search history.

(56) References Cited

U.S. PATENT DOCUMENTS

| 3,508,285 A | * | 4/1970 | Marquette | A47G 9/023 5/923 |
| 5,007,125 A | * | 4/1991 | Owenby | A47G 9/0207 5/482 |
| 2005/0273930 A1 | | 12/2005 | Phillipps | |
| 2006/0282950 A1 | * | 12/2006 | Shuster | A47G 9/0246 5/486 |
| 2009/0044336 A1 | * | 2/2009 | Jackson | A47G 9/0207 5/486 |

(Continued)

FOREIGN PATENT DOCUMENTS

| ES | 1031248 U | * | 9/1995 | ............... A47G 9/02 |
| NL | 1042257 | | 8/2018 | |

OTHER PUBLICATIONS

"Warmth." Merriam-Webster, Merriam-Webster, www.merriam-webster.com/dictionary/warmth.*

(Continued)

*Primary Examiner* — David R Hare
*Assistant Examiner* — Madison Emanski
(74) *Attorney, Agent, or Firm* — Brion Raffoul

(57) ABSTRACT

A bed covering system adapted to be used by a user to stay comfortable during sleep. The bed covering system includes a blanket and a pillowcase. The blanket has different heat retention zones of at least one section of heavy material and at least one section of lighter material. The heavy material is of material that retains body heat of the user. The lighter material is of a material that allows the escape of body heat of the user and allows circulation of body heat of the user. The heavy material has a higher weave count to trap and retain heat, and the lighter material is of thinner materials that permits more evaporation from a body of a user than the heavy material.

18 Claims, 11 Drawing Sheets

(56) References Cited

U.S. PATENT DOCUMENTS

2012/0096642 A1    4/2012  Hickman
2018/0103783 A1*  4/2018  Danaher .............. D03D 13/008

OTHER PUBLICATIONS https://us.amazon.com/Split-Sheets-Sheet-Set-Queen/dp/B0010ZH2QO?_encoding=UTF8&pd_rd_i=B0010ZH2QO&pd_rd_r=24c1be43-16e3-4fd2-b9ca-99533b5ad1f1&pd_rd_w=rAIRK&pd_rd_wg=mGZem&pf_rd_p=5873ae95-9063-4a23-9b7e-eafa738c2269&pf_rd_r=RW1GXV46ZG65D6PBH2K8&psc=1.
https://solvedthat.com/half-bed-sheets-split-sheets/ Solved That, Half Bed Sheets | Split The Sheets, Nov. 7, 2016.

* cited by examiner

BED COVERING SYSTEM

BACKGROUND

The present invention generally relates to bed coverings. More specifically, the present invention relates to a bed covering system of blankets and pillowcases that allows for a range of body temperatures.

Human body temperature varies from the head down to the feet, as illustrated by FIG. 1. FIG. 1 shows temperatures of body 10 when the surrounding temperature is cool room conditions in the range of 65° F. to 74° F. Average temperature of human body is 98.6 F. and is the source of heat under the blanket. FIG. 1 shows temperatures of body 12 when the surrounding temperature is warm room conditions in the range of 74° F. to 80° F. As humans sleep at night, certain parts of the body like the neck, shoulders, hips and feet react differently to temperature fluctuation than the rest of the body. Therefore, covering your body with a blanket or a quilt might keep certain parts of your body comfortable but not other parts, due to the body's temperature variations and its sensitivity to "Hot or Cold". In the past, a person has no choice but to bundle up with covers and shed them at night when they get too warm, or go to sleep with one sheet to find out that it gets cooler at night. Unfortunately nothing in the market today is available to address this problem or solve it.

It is an object of the present invention to provide a bed cover system that conforms to body temperature.

SUMMARY

A bed covering system adapted to be used by a user to stay comfortable during sleep. The bed covering system includes a blanket and a pillowcase. The blanket has different heat retention zones of at least one section of heavy material and at least one section of lighter material. The heavy material is of material that retains body heat of the user. The lighter material is of a material that allows the escape of body heat of the user and allows circulation of body heat of the user. The heavy material has a higher weave count to trap and retain heat, and the lighter material is of thinner materials that permits more evaporation from a body of a user than the heavy material.

DETAILED DESCRIPTION

The present invention is a bed covering system that includes blanket embodiments and pillowcases embodiments. The bed covering system provides for a comfortable sleep by addressing the issues encountered by a person using blankets and pillowcases while dealing with the body's temperature variations and sensitivity to "Hot or Cold". The bed covering system covers certain parts of the body with one cover that has with heavier materials for the parts of the body that need warmth and with lighter materials for parts of the body that do not need as much warmth retention. The bed covering system conforms to body temperature in relation to room temperature conditions. The bed covering system uses heat transfer and circulation principals.

Where using the concept that temperature tends to flow from the warmer surface to the cooler ones, the bed covering system uses the process of heat flow circulation to make sleep comfortable from the head down to feet, without the need to wake up at night to add or delete more covers when feeling either too hot or chilled at night.

The bed cover system is to be used for cool room temperatures (range 65° F. to 74° F.) and warm room temperatures (74° F. to 80° F.). The bed cover system includes the use of heavy materials such as fleece and lighter materials such as cotton. Whereby the heavy materials retain more body heat near the body and the lighter material allow the dispersion of body heat away from the body. The heavy materials will have a higher weave count. The tightly woven fabrics are warmer because they are less permeable to air and thus prevent convective heat loss. The higher the weave count, the thicker the fabric material, therefore, the material can retain and trap more heat, which in turn keeps a user warm. The heavy materials can be express in terms of ounces per square yard. The heavy materials will be in a range of 7-14 oz per square yard or 100-400 grams per square meter (gms). The lighter material is measured by thread count, where thinner materials permit more evaporation from a body of a user. The thread count range used for the lighter materials is 200-400 thread count to allow for greater air flow through the materials.

Figure 1:
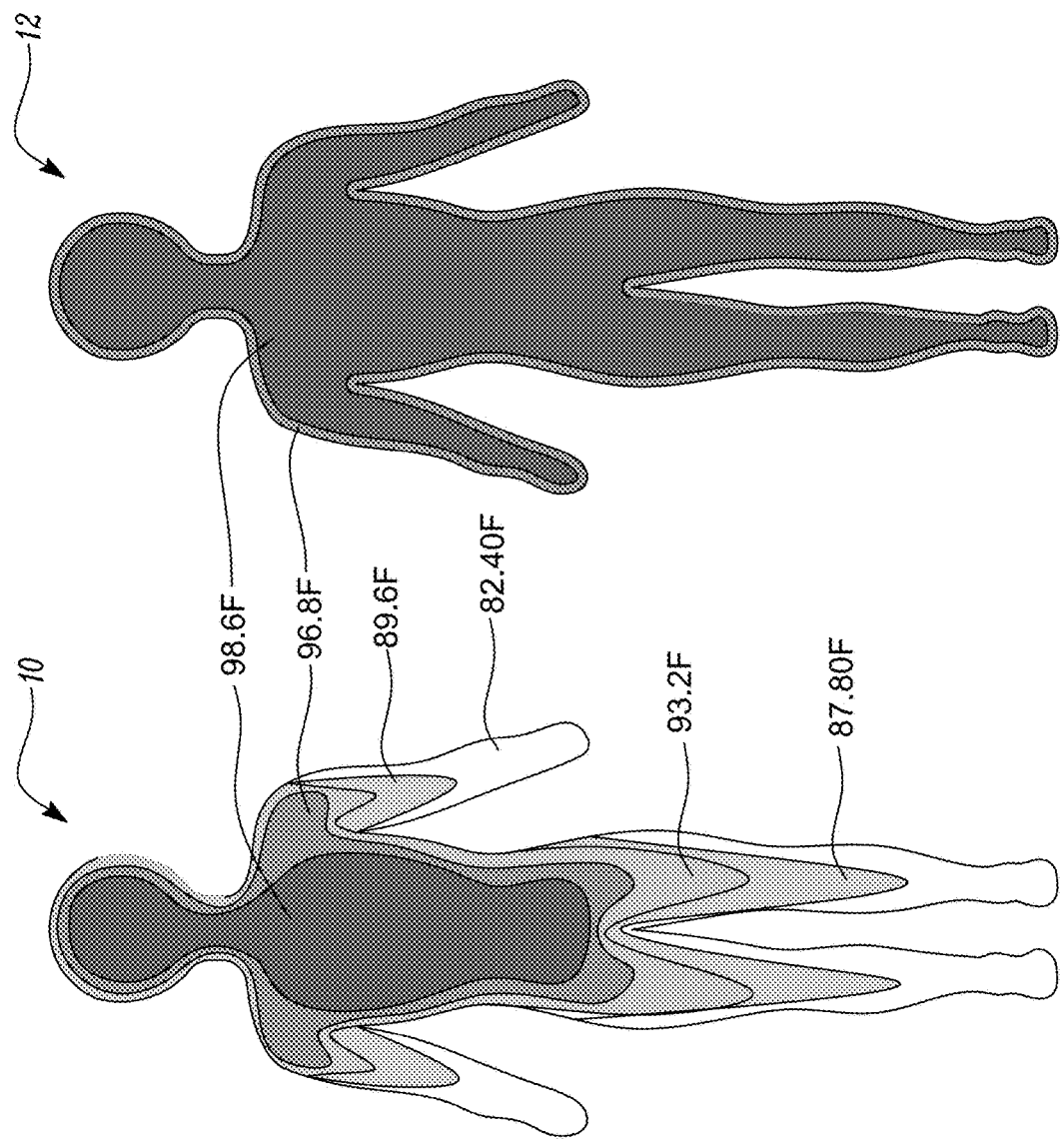
FIG. 1 is a schematic of body temperatures according to the present invention.
Figure 2:
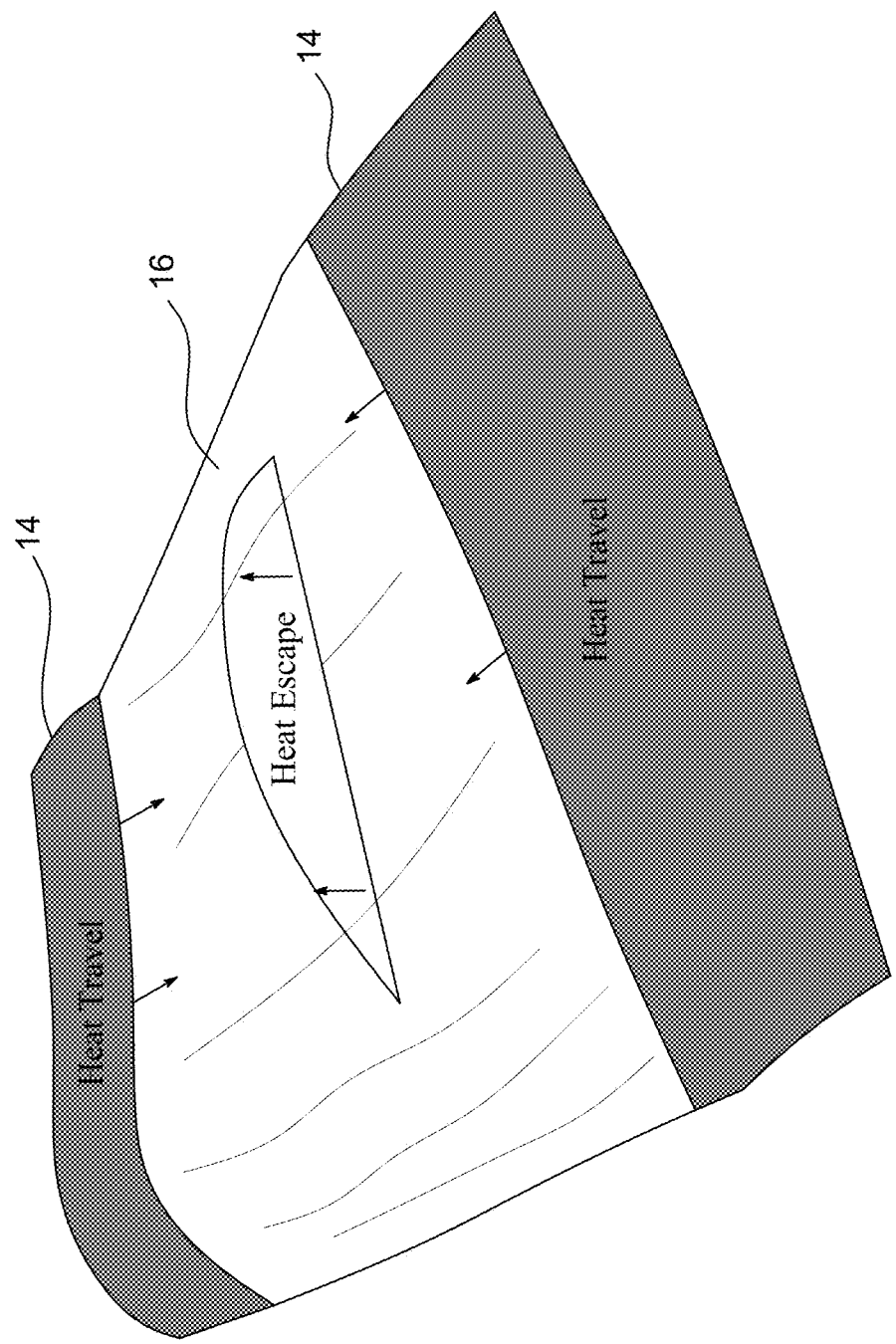
FIG. 2 is a schematic of a cool blanket according to the present invention.
Figure 3:
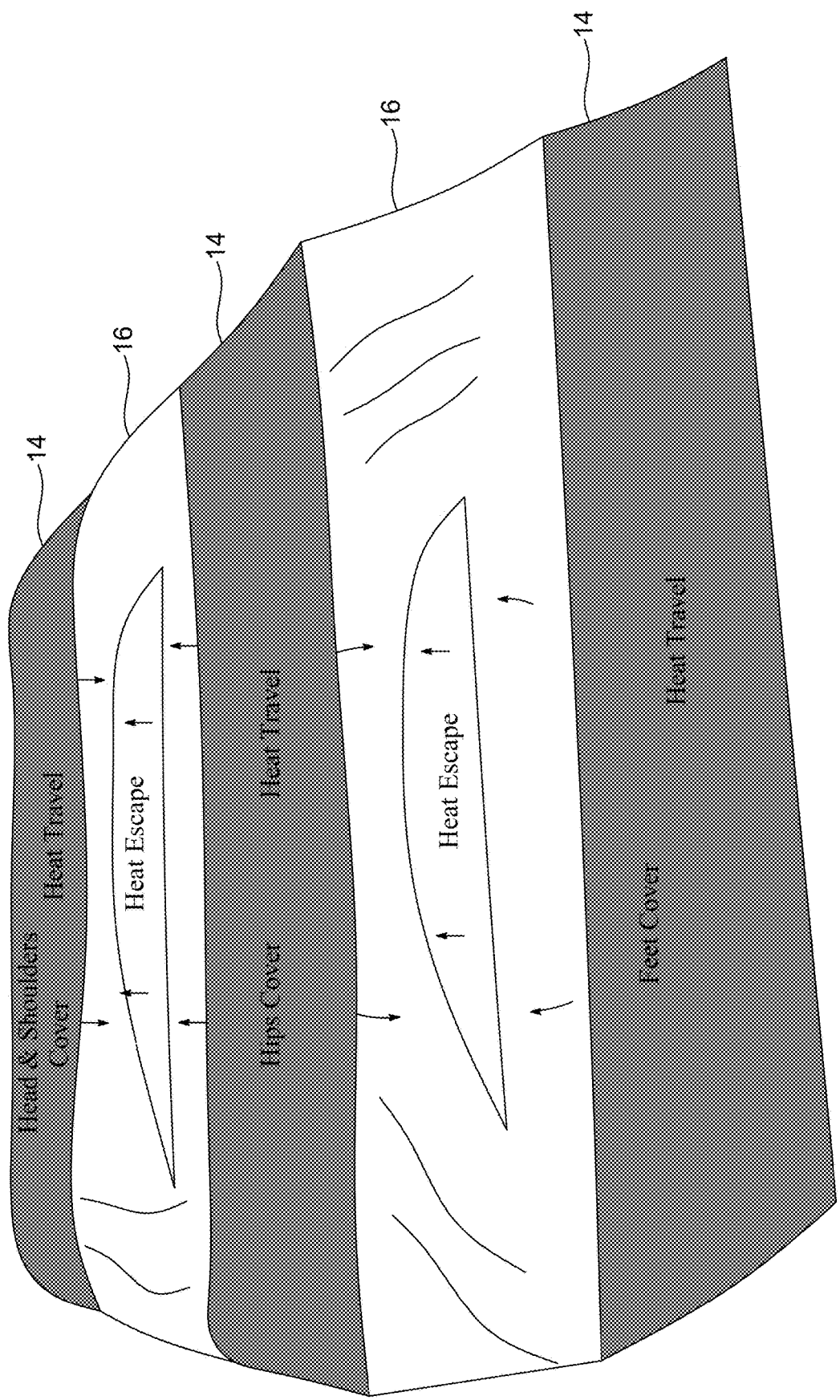
FIG. 3 is a schematic of a warm blanket according to the present invention.
Figure 4:
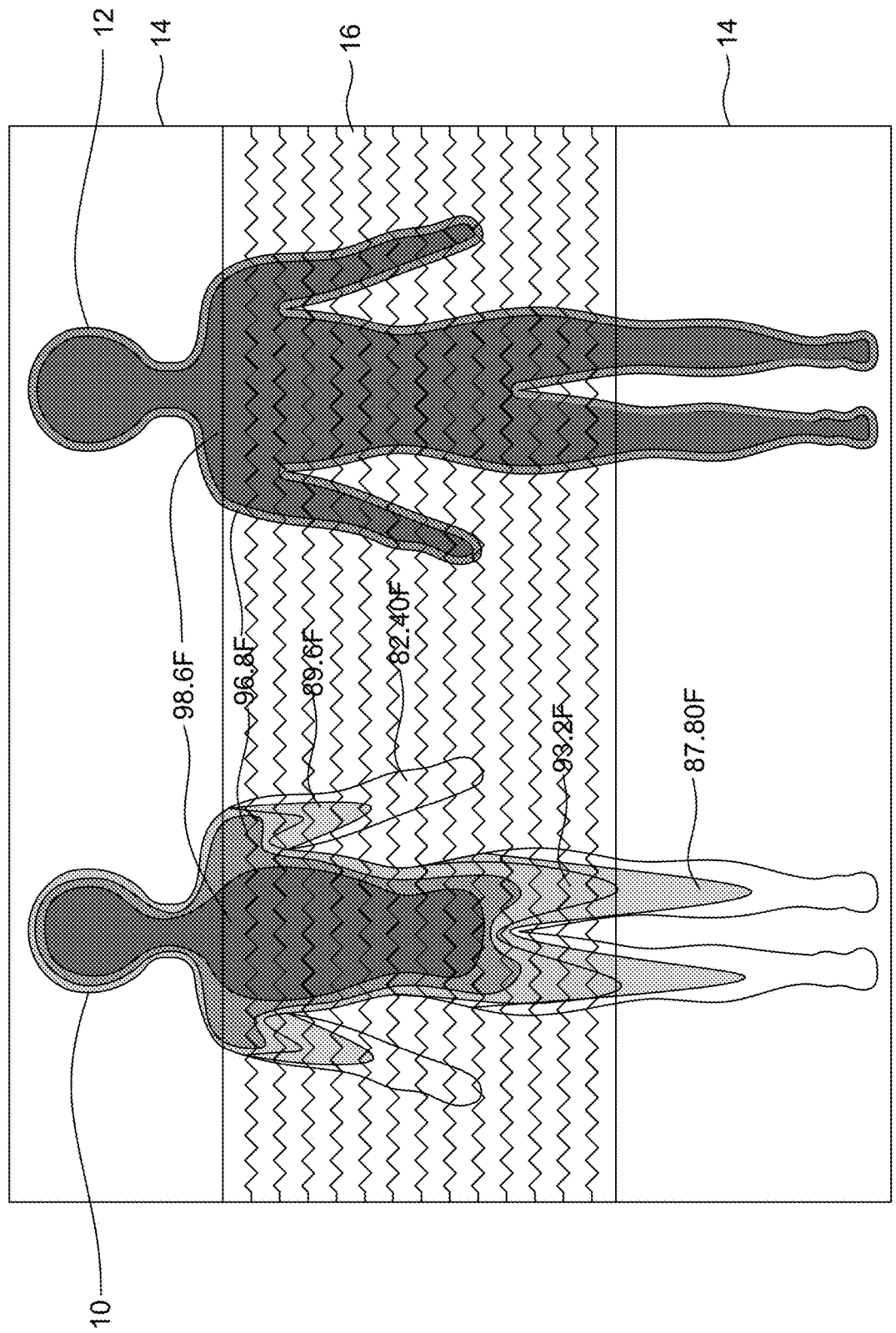
FIG. 4 is a schematic of a cool blanket and body temperatures according to the present invention.
Figure 5:
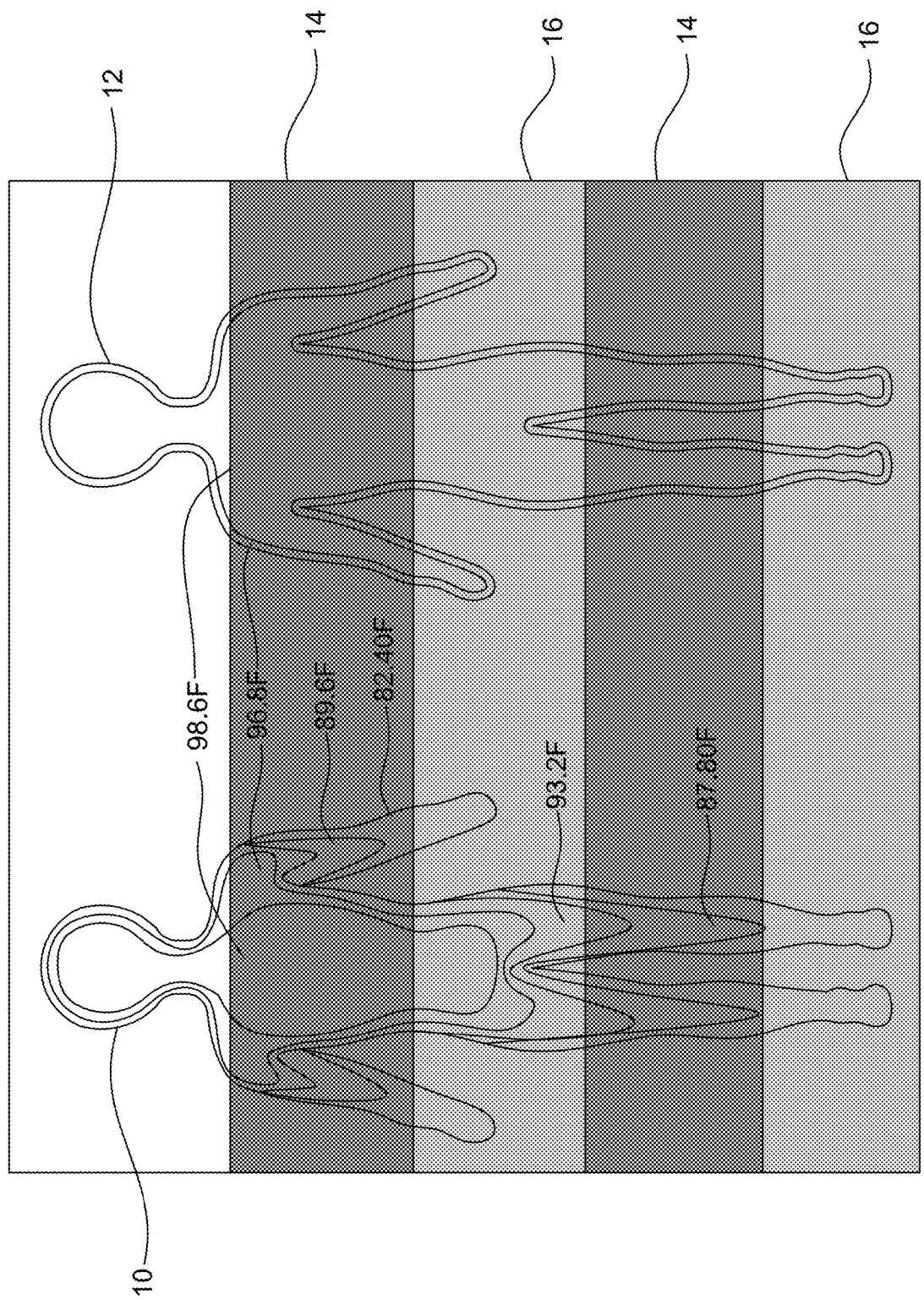
FIG. 5 is a schematic of a warm blanket and body temperatures according to the present invention.
Figure 6:
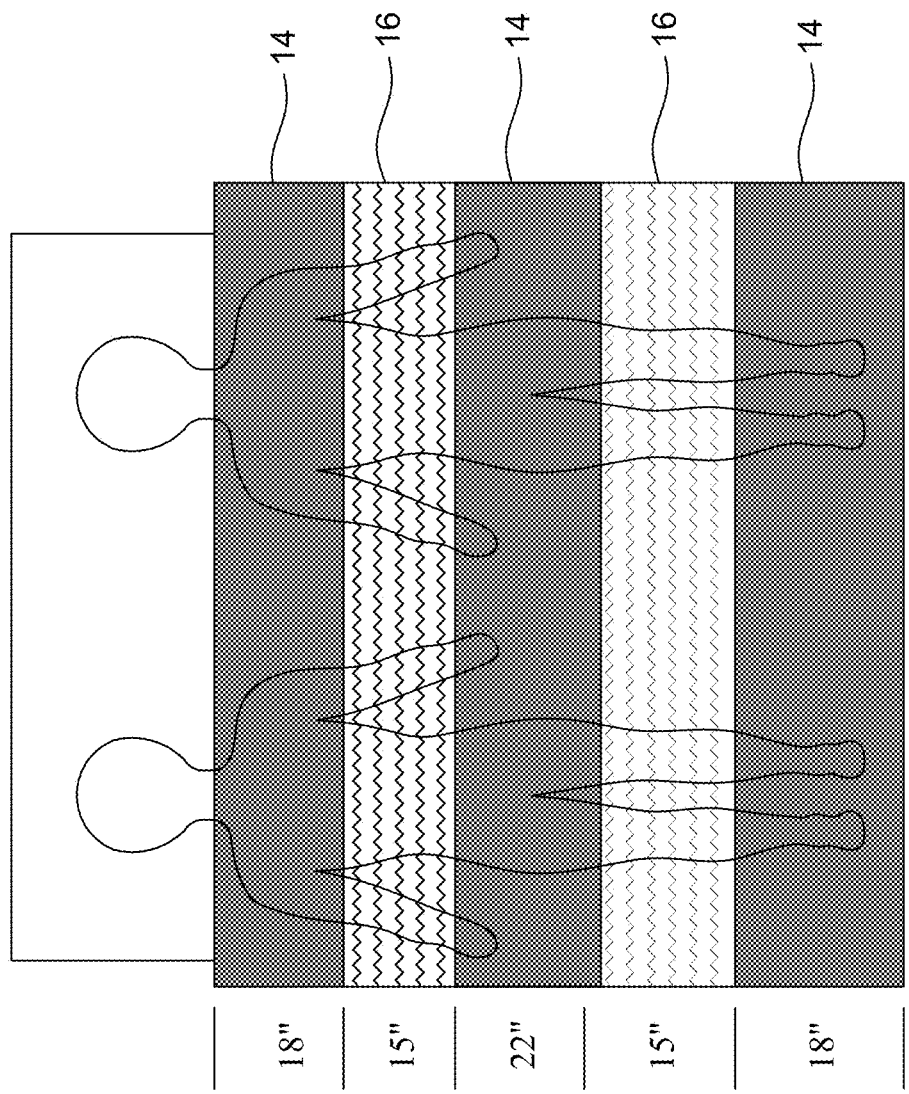
FIG. 6 is a schematic of a warm blanket according to the present invention.
Figure 8:
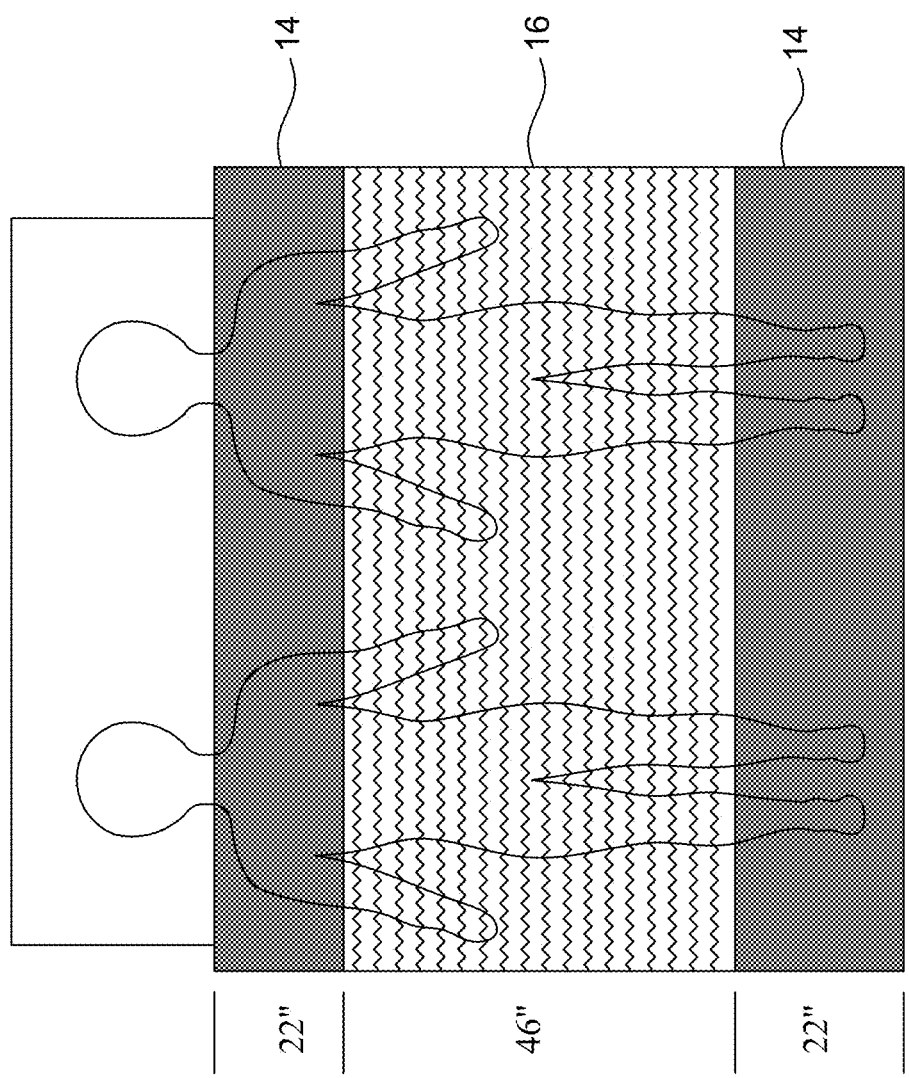
FIG. 8 is a schematic of a cool blanket according to the present invention.
Figure 9:
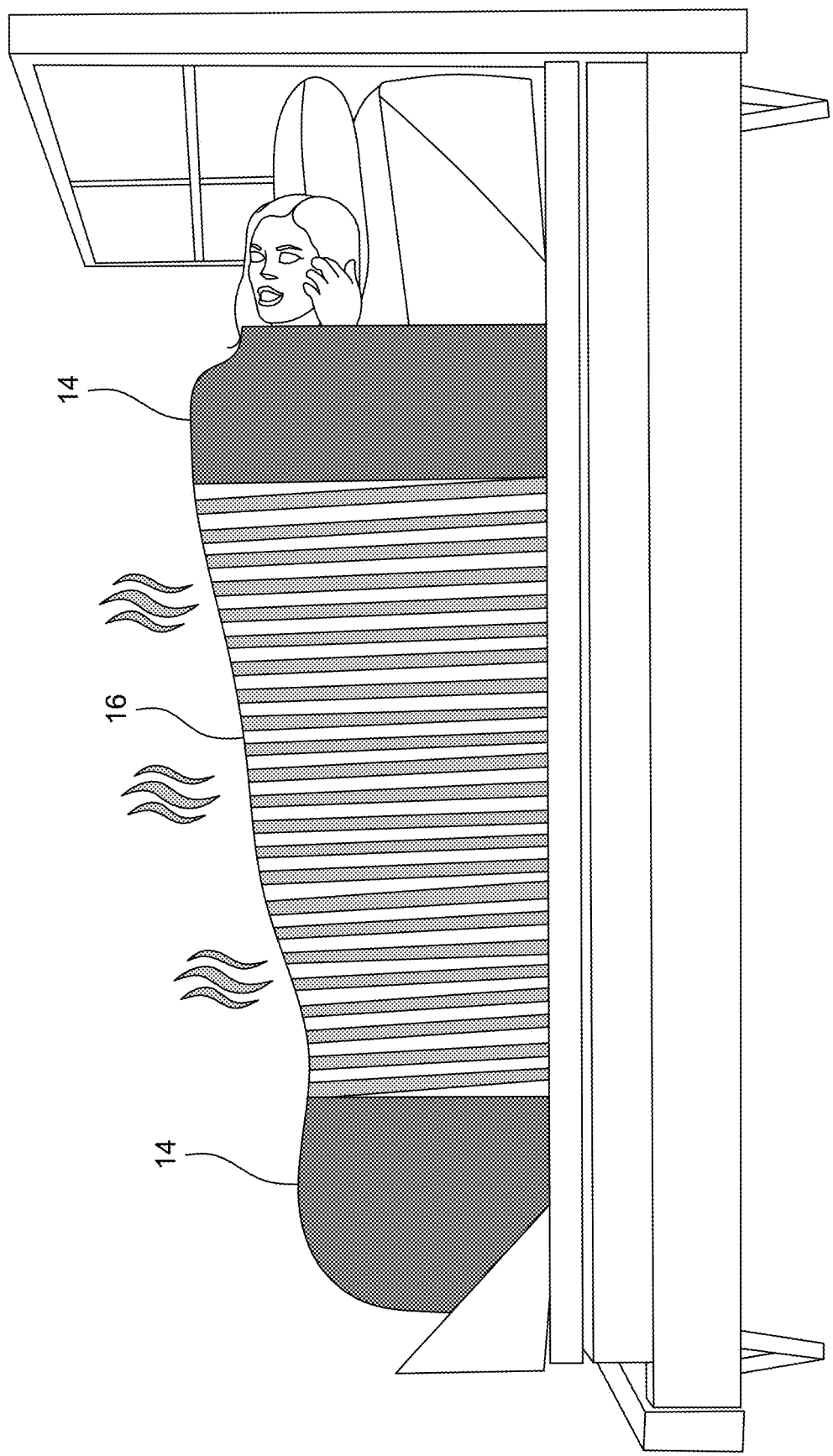
FIG. 9 is a side view of a cool blanket according to the present invention

FIG. 2 shows a blanket embodiment to use for warm room temperatures and is referred to as a cool blanket. The blanket is shown made up of two sections of the heavy material 14 and one section of the lighter material 16. Arrows show body heat traveling from the heavy material 14 towards the lighter material 16 and body heat escaping from the lighter material 16. FIG. 3 shows a blanket embodiment to use for cool room temperatures and is referred to as a warm blanket. The blanket is shown made up of three sections of the heavy material 14 and two sections of the lighter material 16. Arrows show body heat traveling from the heavy material towards the lighter material 16 and body heat escaping from the lighter material 16. FIG. 4 shows the cool blanket superimposed over the bodies of FIG. 1 to cover sensitive areas like the neck & shoulders and the feet but not the less sensitive hips area. FIG. 5 shows the warm blanket superimposed over the bodies of FIG. 1 to cover sensitive areas like the neck & shoulders, hips and feet. Heavy materials 14 can include any type of Fleece, Wool, Chenille, Cotton, Corduroy, Suede, Mink, Polyester, Acrylic, Luxe, Microfiber and Sherpa (Faux Sheepskin or Shearling) or any combination or future fabrics. Lighter materials 16 can include Cotton, Flannel, Bamboo, Bamboo/Cotton, Bamboo/Rayon, Bamboo/Polyester, Cotton/Polyester, Cotton/Rayon, Nylon/Polyester, Linen, Silk and Microfiber or any combination or future fabrics. FIG. 6 shows a warm blanket over bodies of FIG. 1 that includes an example of dimensions for the heavy materials 14 and the lighter materials 16. FIG. 8 shows a cool blanket over bodies of FIG. 1 that includes an example of approximate dimensions for the heavy materials 14 and the lighter materials 16. FIG. 9 shows the cool blanket with heat escaping where it needs to escape. The approximate dimensions for the cool blanket FIG. 8 are top 22" heavy material 14, bottom 22" heavy material 14 and 46" for the middle lighter material 16. The approximate dimensions for the warm blanket FIG. 6 are top 18", middle 22" and bottom 18" heavy material 14 with lighter material 16 both at 15" width. Ratios for how much heavy material 14 to lighter material 16 can be used. For the cool blanket there is lighter material 16 to heavy material 14 in the range of about 60/40±10 percent. For the warm blanket there is lighter material 16 to heavy material 14 in the range of about 20/80±10 percent. The dimensions and ratios can be applied to Twin, Twin XL, Double, Queen, King and California King size blankets.

Figure 10:
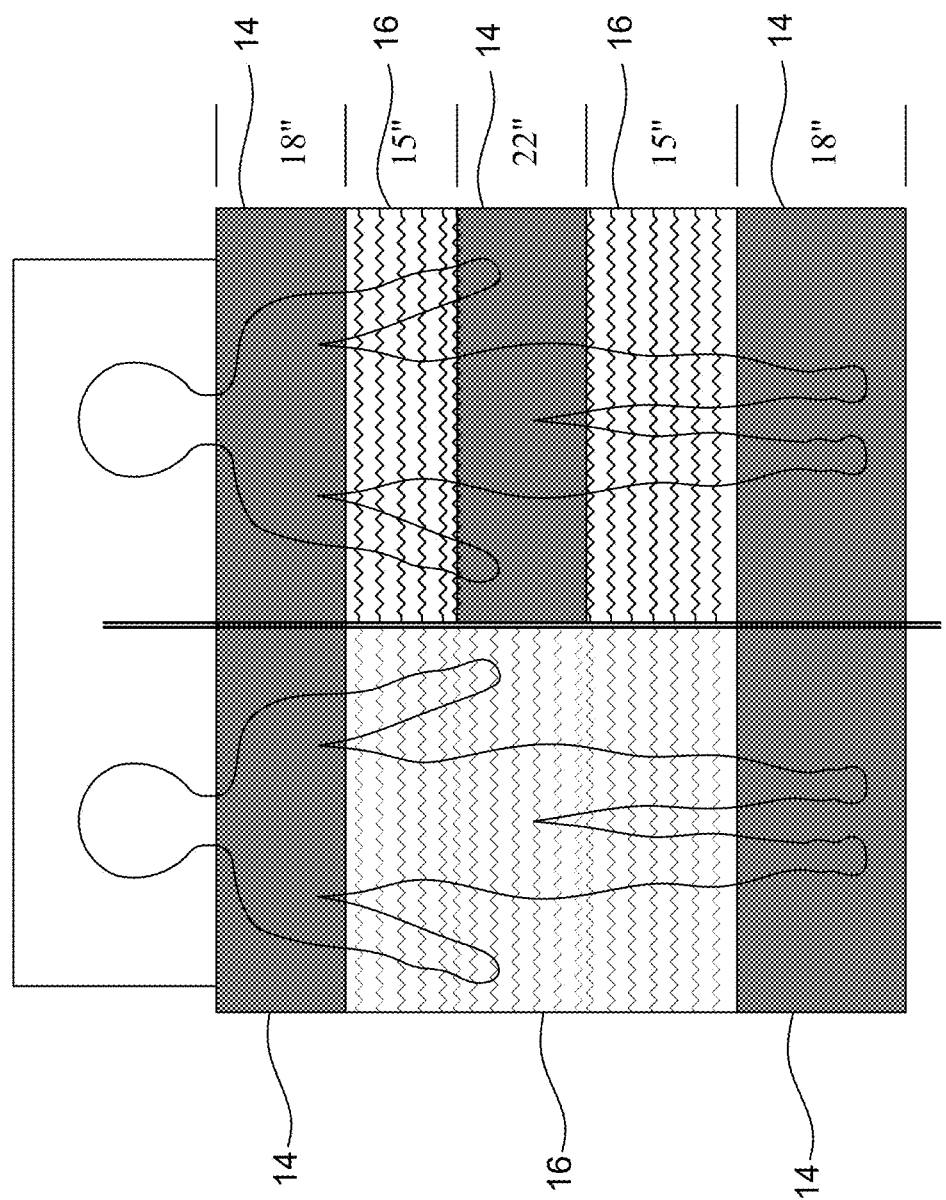
FIG. 10 is a schematic of a combo warm and cool blanket according to the present invention.
Figure 11:
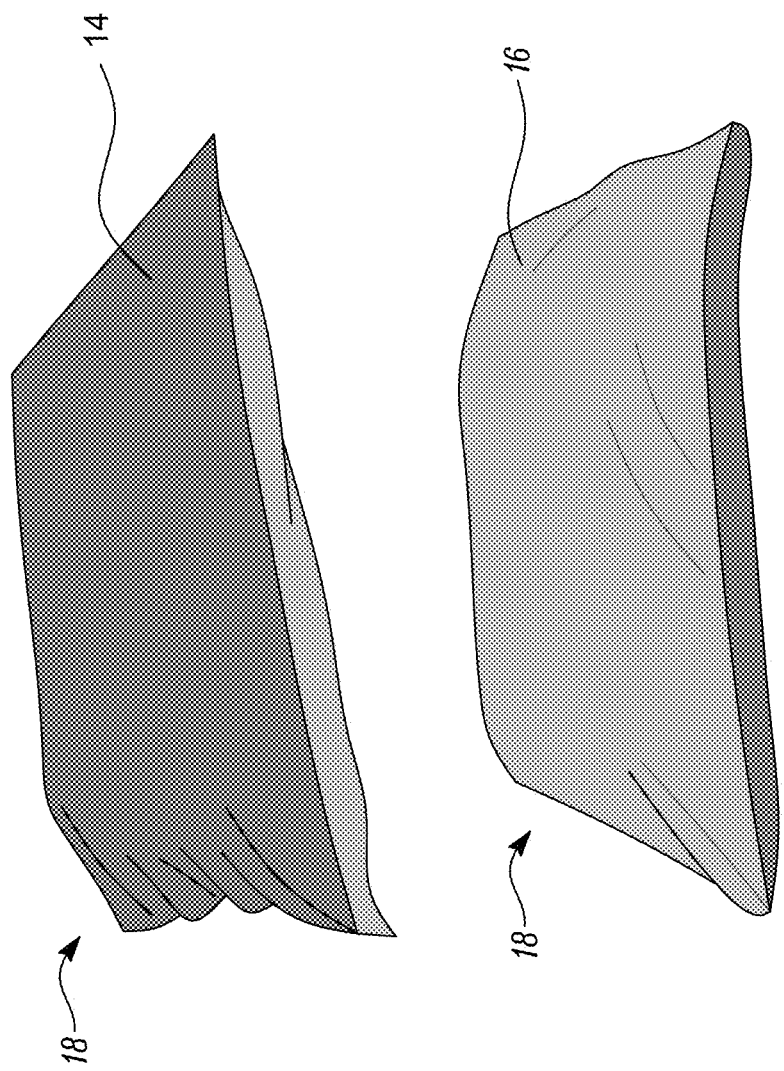
FIG. 11 is a schematic of a pillowcase according to the present invention.

FIG. 10 shows a version that is split with half of the blanket having the attributes of the warm blanket and the other half having the attributes of the cool blanket. FIG. 11 shows a pillowcase covering 18 having the heavier material 14 on one side for cooler room temperatures and having a lighter material 16 on the other side for warmer room temperatures.

Figure 7:
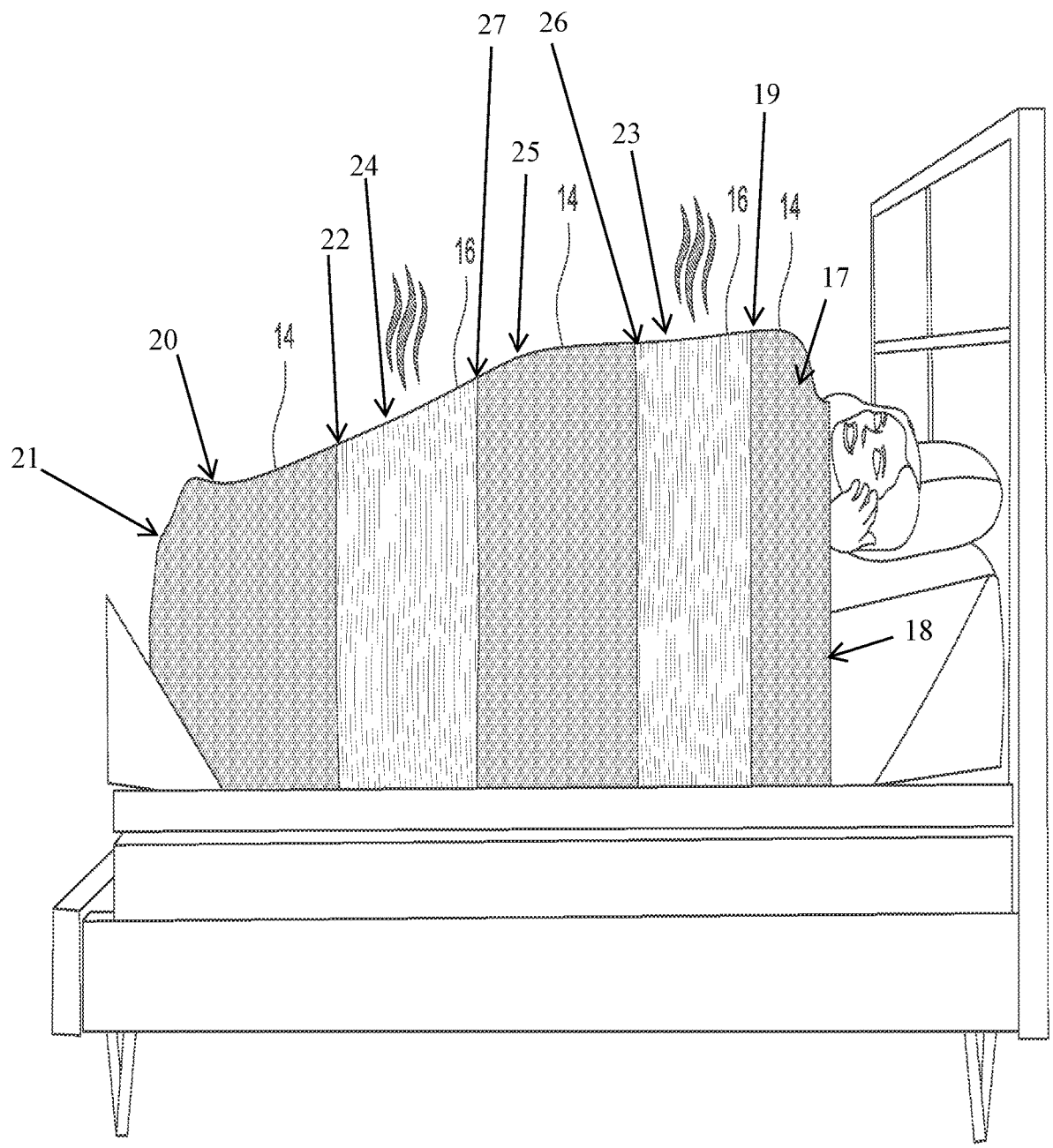
FIG. 7 is a side view of a warm blanket according to the present invention.

Referring to FIG. 7, it can be seen that a blanket according to one aspect of the present invention has different heat retention zones. The blanket has a first section 17 of heavy material. This first section 17 extends from a top latitudinal edge 18 of the blanket to a first internal latitudinal edge 19. The blanket has a second section 20 of heavy material, with the second section extending from a bottom latitudinal edge 21 of the blanket to a second internal latitudinal edge 22. The blanket also has a third section with one or more subsections of lighter material. This third section extends from the first internal latitudinal edge 19 to the second internal latitudinal edge 22. In this embodiment, the third section has two subsections 23, 24 of lighter material and a single subsection 25 of heavy material. The single subsection 25 of heavy material is between the two subsections 23, 24 of lighter material. As can be seen from FIG. 7, the single subsection 25 of heavy material extends from a third internal latitudinal edge 26 to a fourth internal latitudinal edge 27. Of the two subsections of lighter material, the first subsection 23 extends from the first internal latitudinal edge 19 to the third internal latitudinal edge 26. The second subsection 24 of lighter material extends from the fourth internal latitudinal edge 27 to the second internal latitudinal edge 22.

While different embodiments of the invention have been described in detail herein, it will be appreciated by those skilled in the art that various modifications and alternatives to the embodiments could be developed in light of the overall teachings of the disclosure. Accordingly, the particular arrangements are illustrative only and are not limiting as to the scope of the invention that is to be given the full breadth of any and all equivalents thereof.

We claim:

1. A bed covering system adapted to be used by a user to stay comfortable during sleep, comprising of
    a blanket having different heat retention zones the blanket comprising:
        a first section of heavy material, said first section extending from a top latitudinal edge of said blanket to a first internal latitudinal edge;
        a second section of said heavy material, said second section extending from a bottom latitudinal edge of said blanket to a second internal latitudinal edge; and
        a third section comprising one or more subsections of lighter material, said third section extending from said first internal latitudinal edge to said second internal latitudinal edge;
    wherein
    said heavy material being a first material that retains body heat of the user; and
    said lighter material being a second material that allows an escape of body heat of the user and allows circulation of body heat of the user;
    said third section comprises two subsections of lighter material and a single subsection of heavy material, said single subsection of heavy material being between said two subsections of lighter material.

2. The bed covering system of claim 1, wherein said heavy material has a higher weave count to trap and retain heat, and wherein said lighter material is a thinner material that permits more evaporation from a body of a user than said heavy material.

3. The bed covering system of claim 2, wherein said heavy material is in the range of 7-14 oz. per square yard and wherein said lighter material has a thread count in the range of a 200-400 thread count.

4. The bed covering system of claim 3, wherein, for said first section, a longitudinal distance from said top latitudinal edge to said first internal latitudinal edge is 22 inches, and wherein, for said second section, a longitudinal distance from said bottom latitudinal edge to said second internal latitudinal edge is 22 inches and wherein, for said third section, a longitudinal distance from said first internal latitudinal edge to said second internal latitudinal edge is 46 inches.

5. The bed covering system of claim 3, wherein said blanket has lighter material sections to heavy material sections in the range of about 60/40±10 percent.

6. The bed covering system of claim 3, wherein said blanket has lighter material sections to heavy material sections in the range of about 20/80±10 percent.

7. The bed covering system of claim 2, wherein, for said first section, a longitudinal distance from said top latitudinal edge to said first internal latitudinal edge is 22 inches, and wherein, for said second section, a longitudinal distance from said bottom latitudinal edge to said second internal latitudinal edge is 22 inches and wherein, for said third section, a longitudinal distance from said first internal latitudinal edge to said second internal latitudinal edge is 46 inches.

8. The bed covering system of claim 2, wherein said blanket has lighter material sections to heavy material sections in the range of about 60/40±10 percent.

9. The bed covering system of claim 2, wherein said blanket has lighter material sections to heavy material sections in the range of about 20/80±10 percent.

10. The bed covering system of claim 2, further including a pillowcase covering having one side of a heavy material and the other side of a lighter material.

11. The bed covering system of claim 1, wherein, for said first section, a longitudinal distance from said top latitudinal edge to said first internal latitudinal edge is, and wherein, for said second section, a longitudinal distance from said bottom latitudinal edge to said second internal latitudinal edge is 22 inches and wherein, for said third section, a longitudinal distance from said first internal latitudinal edge to said second internal latitudinal edge is 46 inches.

12. The bed covering system of claim 1, wherein said blanket has lighter material sections to heavy material sections in the range of about 60/40±10 percent.

13. The bed covering system of claim 1, wherein said blanket has lighter material sections to heavy material sections in the range of about 20/80±10 percent.

14. The bed covering system of claim 1, further including a pillowcase covering having one side of a heavy material and the other side of a lighter material.

15. The bed covering system of claim 1,
wherein said single subsection of heavy material extends from a third internal latitudinal edge to a fourth internal latitudinal edge and
wherein a first subsection of said two subsections of lighter material extends from said first internal latitudinal edge to said third internal latitudinal edge and
wherein a second subsection of said two subsections of lighter material extends from said fourth internal latitudinal edge to said second internal latitudinal edge.

16. The bed covering system of claim 15 wherein
said top latitudinal edge is separated from said first internal latitudinal edge by a longitudinal distance of 18 inches; and
said bottom latitudinal edge is separated from said second internal latitudinal edge by a longitudinal distance of 18 inches.

17. The bed covering system of claim 15 wherein said third internal latitudinal edge is separated from said fourth latitudinal edge by a longitudinal distance of 22 inches.

18. The bed covering system of claim 15 wherein
said first internal latitudinal edge is separated from said third internal latitudinal edge by a longitudinal distance of 15 inches and
said second internal latitudinal edge is separated from said fourth internal latitudinal distance by a longitudinal distance of 15 inches.

* * * * *